United States Patent [19]

Wakefield et al.

[11] Patent Number: 5,721,212

[45] Date of Patent: *Feb. 24, 1998

[54] PEPTIDES FOR HEPARIN AND LOW MOLECULAR WEIGHT HEPARIN ANTICOAGULATION REVERSAL

[75] Inventors: Thomas W. Wakefield; James C. Stanley; Philip C. Andrews, all of Ann Arbor, Mich.

[73] Assignee: University of Michigan, The Board of Regents . . . et al., Ann Arbor, Mich.

[*] Notice: The term of this patent shall not extend beyond the expiration date of Pat. No. 5,534,619.

[21] Appl. No.: 677,304

[22] Filed: Jul. 9, 1996

Related U.S. Application Data

[62] Division of Ser. No. 152,488, which is a continuation-in-part of PCT/US92/06829, Aug. 14, 1992, Pat. No. 5,534,619.

[51] Int. Cl.⁶ .......................... A61K 38/00; C07K 14/00
[52] U.S. Cl. ................................ 514/12; 530/324
[58] Field of Search .................... 514/12, 2, 13; 530/300, 324, 326

[56] References Cited

U.S. PATENT DOCUMENTS 4,792,525 12/1988 Ruoslahti et al. .
5,272,261 12/1993 Cardin et al. .
5,358,934 10/1994 Borovsky et al. .

*Primary Examiner*—Paula K. Hutzell
*Assistant Examiner*—Benet Prickril
*Attorney, Agent, or Firm*—Miller, Canfield, Paddock and Stone, P.L.C.

[57] ABSTRACT

Less toxic agents for reversal of heparin or low molecular weight heparin anticoagulation which are synthetic protamine-like polycationic peptides having a total cationic charge which is less than that of n-protamine. In preferred embodiments, arginine resides of n-protamine are replaced with lysine residues for ease of manufacture. Selective positively charged arginine residues have been replaced with an uncharged amino acid residue or its analog, such as glycine or glutamine, in order to reduce the total cationic charge on the polycationic peptide to the range of about [+14] to [+18], preferably [+16]. In specific embodiments, there are sequences of 29 amino acid residues wherein 4 to 5 clusters of 2 to 4 positively charged amino acids are separated by 2 to 6 neutral amino acids. The C-terminus and the N-terminus can be modified to mitigate against in vivo degradation by carboxypeptidases and aminopeptidases.

17 Claims, 4 Drawing Sheets

ACTIVATED CLOTTING TIME

THROMBIN CLOTTING TIME

FACTOR Xa HEPARIN ACTIVE ASSAY

FACTOR IIa HEPARIN ACTIVE ASSAY

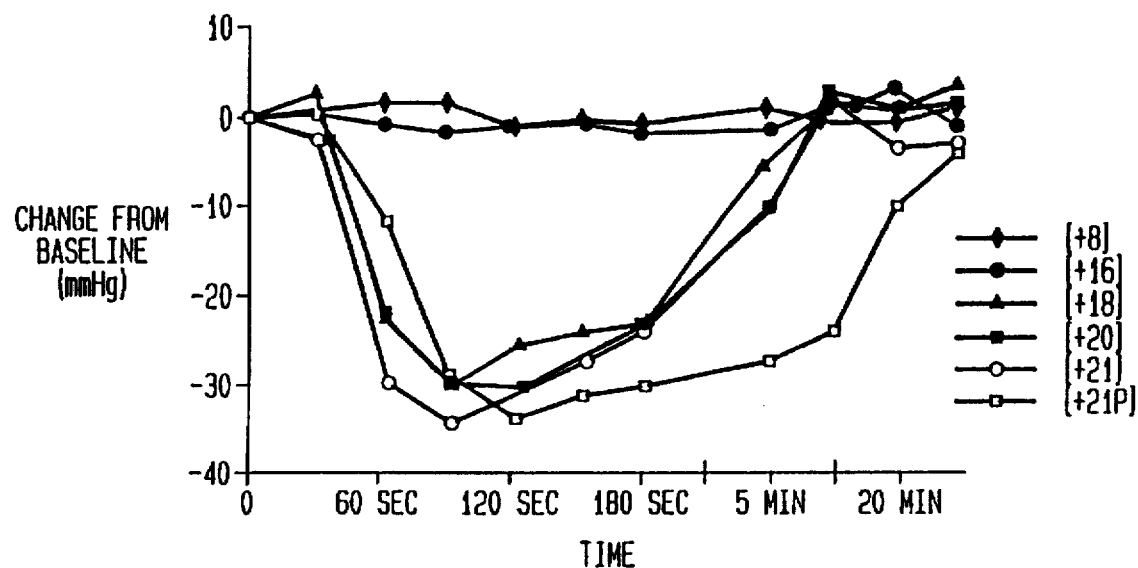
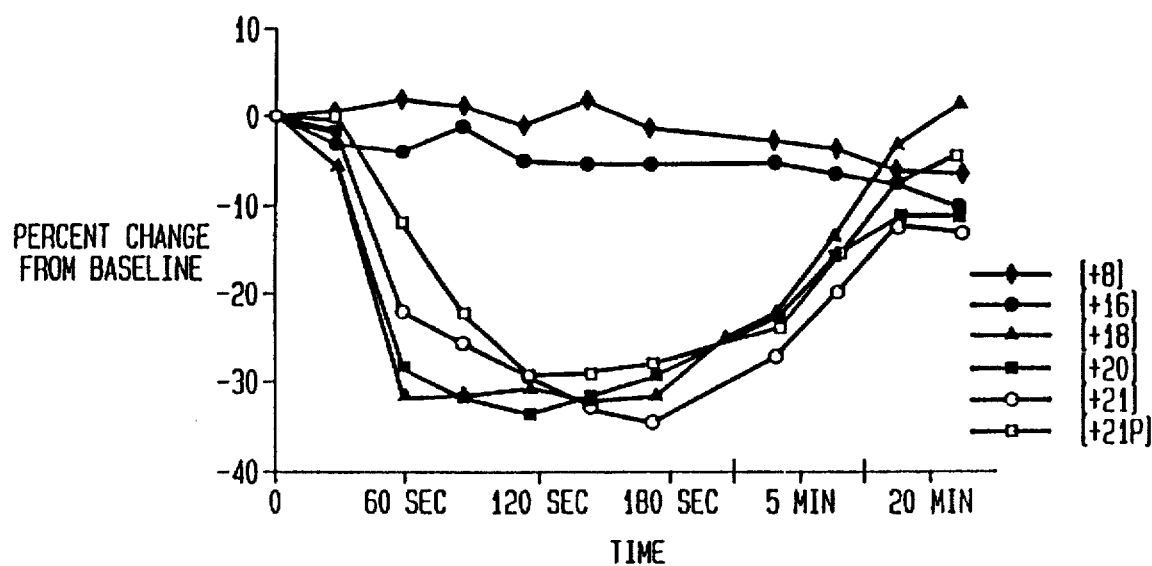

TOTAL TOXICITY SCORES OF PEPTIDE VARIANTS

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: N/A ( x ) PUBLICATION INFORMATION:
        ( A ) AUTHORS: N/A
        ( B ) TITLE: N/A ( x ) PUBLICATION INFORMATION:
        ( H ) DOCUMENT NUMBER: PCT/US92/08069
        ( I ) FILING DATE: 14-AUG- 1993

( x i ) SEQUENCE DESCRIPTION: SEQ ID NO:1:

```
Pro Lys Lys Gln Gln Gly Gly Gly Gly Lys Lys Gln Gln Gly Gly
1               5                   10                  15
Gly Gly Lys Lys Gln Gln Gly Gly Gly Gly Lys Lys Gln Gln
                20                  25
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: N/A ( x ) PUBLICATION INFORMATION:
        ( A ) AUTHORS: N/A
        ( B ) TITLE: N/A ( x ) PUBLICATION INFORMATION:
        ( H ) DOCUMENT NUMBER: PCT/US92/08069
        ( I ) FILING DATE: 14-AUG- 1993

( x i ) SEQUENCE DESCRIPTION: SEQ ID NO:2:

```
Pro Lys Gly Lys Gly Lys Gly Lys Gly Lys Gly Lys Gly Lys Gly
1               5                   10                  15
Lys Gly Lys Gly Lys Gly Lys Gly Lys Gly Lys Gly Lys
                20                  25
```

( 2 ) INFORMATION FOR SEQ ID NO:3:

( i ) SEQUENCE CHARACTERISTICS:
        ( A ) LENGTH: 29 amino acids (B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: N/A (x) PUBLICATION INFORMATION:
(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:3:

Thr Pro Lys Ala Lys Ala Lys Ala Lys Ala Lys Ala Lys Ala Lys Ala
                 5                  10                  15
Lys Ala Lys Ala Lys Ala Lys Ala Lys Ala Lys Ala Lys
             20                  25

(2) INFORMATION FOR SEQ ID NO:4:

(i) SEQUENCE CHARACTERISTICS:
(A) LENGTH: 29 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: N/A (x) PUBLICATION INFORMATION:
(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:4:

Pro Lys Lys Lys Lys Gly Gly Gly Gly Lys Lys Lys Lys Gly Gly Gly
                 5                  10                  15
Gly Lys Lys Lys Lys Gly Gly Gly Gly Lys Lys Lys Lys
             20                  25

(2) INFORMATION FOR SEQ ID NO:5:

(i) SEQUENCE CHARACTERISTICS:
(A) LENGTH: 29 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: N/A (x) PUBLICATION INFORMATION:
(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:5:

Pro Lys Lys Lys Lys Gly Gly Gly Gly Lys Lys Lys Lys Gly Gly

```
                      5                         10                        15
Lys  Lys  Lys  Lys  Gly  Gly  Lys  Lys  Lys  Lys  Gly  Gly  Lys  Lys
                              20                        25
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: N/A (x) PUBLICATION INFORMATION:
        (A) AUTHORS: N/A
        (B) TITLE: N/A (x) PUBLICATION INFORMATION:
        (H) DOCUMENT NUMBER: PCT/US92/08069
        (I) FILING DATE: 14-AUG-1993

(xi) SEQUENCE DESCRIPTION: SEQ ID NO:6:

```
Pro  Lys  Lys  Gly  Lys  Lys  Gly  Lys  Lys  Gly  Lys  Lys  Gly  Lys  Lys
                    5                        10                        15
Gly  Lys  Lys  Gly  Lys  Lys  Gly  Lys  Lys  Gly  Lys  Lys  Gly  Lys  Lys
                    20                       25                        30
```

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: N/A (x) PUBLICATION INFORMATION:
        (A) AUTHORS: N/A
        (B) TITLE: N/A (x) PUBLICATION INFORMATION:
        (H) DOCUMENT NUMBER: PCT/US92/08069
        (I) FILING DATE: 14-AUG-1993

(xi) SEQUENCE DESCRIPTION: SEQ ID NO:7:

```
Pro  Lys  Lys  Lys  Lys  Gly  Gly  Lys  Lys  Lys  Lys  Gly  Gly  Lys  Lys
                    5                        10                        15
Lys  Lys  Gly  Gly  Lys  Lys  Lys  Lys  Gly  Gly  Lys  Lys  Lys  Lys
                    20                       25
```

(2) INFORMATION FOR SEQ ID NO:8:

(i) SEQUENCE CHARACTERISTICS:
        (A) LENGTH: 32 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: N/A (x) PUBLICATION INFORMATION:

(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:8:

Pro Lys Lys Lys Lys Ser Ser Ser Lys Pro Val Lys Lys Lys Lys
                  5                  10                  15
Lys Pro Lys Val Ser Lys Lys Lys Lys Lys Lys Gly Gly Lys Lys
                 20                  25                  30
Lys Lys (2) INFORMATION FOR SEQ ID NO:9:

(i) SEQUENCE CHARACTERISTICS:
(A) LENGTH: 32 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: N/A (x) PUBLICATION INFORMATION:
(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:9:

Pro Arg Arg Arg Arg Ser Ser Ser Arg Pro Val Arg Arg Arg Arg
                  5                  10                  15
Arg Pro Arg Val Ser Arg Arg Arg Arg Arg Arg Gly Gly Arg Arg
                 20                  25                  30
Arg Arg (2) INFORMATION FOR SEQ ID NO:10:

(i) SEQUENCE CHARACTERISTICS:
(A) LENGTH: 29 amino acids
(B) TYPE: amino acid
(C) STRANDEDNESS: Not Relevant
(D) TOPOLOGY: Not Relevant (ii) MOLECULE TYPE: peptide (vi) ORIGINAL SOURCE:
(A) ORGANISM: N/A (x) PUBLICATION INFORMATION:
(A) AUTHORS: N/A
(B) TITLE: N/A (x) PUBLICATION INFORMATION:
(H) DOCUMENT NUMBER: PCT/US92/08069
(I) FILING DATE: 14-AUG-1993

(xi) SEQUENCE DESCRIPTION: SEQ ID NO:10:

Pro Ala Lys Lys Ala Ala Lys Lys Ala Lys Lys Ala Ala Lys Lys
                  5                  10                  15
Ala Lys Lys Ala Ala Lys Lys Ala Lys Lys Ala Ala Lys Lys
                 20                  25

( 2 ) INFORMATION FOR SEQ ID NO:11:

( i ) SEQUENCE CHARACTERISTICS:
        ( A ) LENGTH: 29 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: N/A ( x ) PUBLICATION INFORMATION:
        ( A ) AUTHORS: N/A
        ( B ) TITLE: N/A ( x ) PUBLICATION INFORMATION:
        ( H ) DOCUMENT NUMBER: PCT/US92/08069
        ( I ) FILING DATE: 14-AUG-1993

( x i ) SEQUENCE DESCRIPTION: SEQ ID NO:11:

Pro Ala Lys Lys Ala Ala Lys Lys Ala Lys Lys Ala Ala Lys
                5                            10
Lys Ala Lys Lys Ala Ala Lys Lys Ala Lys Lys Ala Ala Lys Lys
15              20                    25

( 2 ) INFORMATION FOR SEQ ID NO:12:

( i ) SEQUENCE CHARACTERISTICS:
        ( A ) LENGTH: 29 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: N/A ( x ) PUBLICATION INFORMATION:
        ( A ) AUTHORS: N/A
        ( B ) TITLE: N/A ( x ) PUBLICATION INFORMATION:
        ( H ) DOCUMENT NUMBER: PCT/US92/08069
        ( I ) FILING DATE: 14-AUG-1993

( x i ) SEQUENCE DESCRIPTION: SEQ ID NO:12:

Pro Lys Lys Lys Ala Ala Lys Lys Ala Lys Lys Ala Ala Lys Lys
                5                        10                    15
Ala Lys Lys Ala Ala Lys Lys Ala Lys Lys Ala Lys Lys Lys
                20                    25

( 2 ) INFORMATION FOR SEQ ID NO:13:

( i ) SEQUENCE CHARACTERISTICS:
        ( A ) LENGTH: 32 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: N/A ( x ) PUBLICATION INFORMATION:
        ( A ) AUTHORS: N/A
        ( B ) TITLE: N/A ( x ) PUBLICATION INFORMATION:
        ( H ) DOCUMENT NUMBER: PCT/US92/08069
        ( I ) FILING DATE: 14-AUG-1993

( x i ) SEQUENCE DESCRIPTION: SEQ ID NO:13:

Pro Ala Lys Lys Ala Ala Lys Lys Ala Lys Lys Ala Ala Lys
                    5                   10

Lys Ala Lys Lys Ala Ala Lys Lys Ala Lys Lys Ala Ala Lys Lys Ala
 15                  20                  25                  30

Lys Lys

PEPTIDES FOR HEPARIN AND LOW MOLECULAR WEIGHT HEPARIN ANTICOAGULATION REVERSAL

This is a division of application Ser. No. 08/152,488 filed on Nov. 12, 1993, (U.S. Pat. No. 5,534,169), which is a continuation-in-part of PCT/US92/06829 filed on Aug. 14, 1992, all applications being assigned to the assignee hereof.

BACKGROUND OF THE INVENTION

1. Technical Field

This invention relates generally to agents for reversal of heparin and low molecular weight heparin anticoagulation, and more particularly, to novel peptide compositions which are less toxic variants of protamine.

2. Background of the Prior Art

Heparin, a highly sulfated polyanionic macromolecule comprising a group of polydiverse (molecular weight ranges from 5,000 to 30,000 daltons) straight-chain anionic mucopolysaccharides called glycosaminoglycans, is the most commonly used clinical anticoagulant. Its major clinical applications include, inter alia: treatment of thromboembolism; prophylactic treatment of patients at high risk for embolism; post-operative prevention of thromboembolism; and prevention of clotting and thrombus formation resulting from interventions in the circulatory system, such as cardiovascular diagnostic procedures, catheterization, surgery of the heart and vessels, and many other procedures including extracorporeal blood circulation, such as hemodialysis, use of artificial organs and organ transplantation. At the conclusion of these procedures, the anticoagulation effects of heparin must be neutralized or reversed in order to prevent the patient from bleeding.

Currently, protamine sulfate is the only available compound used to reverse heparin coagulation. Protamine sulfate is a polycationic peptide derived from salmon sperm, sometimes designated salmine protamine or n-protamine. Unfortunately, the use of protamine frequently results in adverse hemodynamic and hematologic side effects such as hypotension, bradycardia, pulmonary artery hypertension, depressed oxygen consumption, thrombocytopenia with pulmonary platelet sequestration, and leukopenia. In clinical use, significant systemic arterial hypertension and pulmonary artery hypertension occur in about 4% of the cases. In some instances, death has resulted. Considering cardiovascular procedures only, more than 450,000 patients per year in the United States can be expected to exhibit protamine related side effects. Furthermore, many patients suffer adverse immunologic reactions to protamine. There is clearly a need for a safer, less toxic agent for reversal of heparin.

The major constituent of protamine is arginine, a highly alkaline cationic substance. Conventional salmine protamine is a mixture of highly cationic peptides. The most prevalent peptide is a 32 amino acid sequence having a total cationic charge of [+21]: ProArg$_4$Ser$_3$ArgProValArg$_5$ProArgValSerArg$_6$Gly$_2$Arg$_4$. (SEQ ID NO:9) Positively charged arginine accounts for 67% of the total sequence and for all of the peptide's positive charge. In this sequence, there are four positively charged arginyl clusters connected by aminoacyl residues.

The efficacy of protamine for heparin neutralization may be, at least in part, a function of its positive charge. There is great potential for ionic interaction between the polycation protamine and the polyanion heparin. The therapeutic effect of standard heparin lies primarily in its ability to enhance inactivation of thrombin (T) by anti-thrombin III (AT-III). Further, heparin potentiates the ability of AT-III to inactivate both factor Xa and factor IIa (thrombin). Two dimensional crossed immunoelectrophoresis studies suggest that protamine dissociates AT-III:heparin complexes by virtue of its positive charge resulting in heparin anticoagulation reversal. When the complex is dissociated, AT-III returns to its unpotentiated state.

Other highly charged polycations, such as poly-I-lysine or polybrene, are capable of neutralizing heparin. However, both poly-I-lysine and polybrene have proven to be too toxic for clinical use. Therefore, the same positive charge which reverses the effect of heparin may be a cause of protamine's toxicity. In vitro data suggest that charge-related events may be toxic due to elaboration of specific vasodilatory factors, disruption of specific cellular organelles such as mitochondria, or by alteration in the pH of the intracellular or intraorganelle matrix.

In addition to unfractionated standard heparin, low-molecular weight heparin, or fractionated heparin, is beginning to find application in the practice of medicine. LMWH has now been recommended for cardiovascular surgery, and may be preferable to standard, unfractionated heparin for bolus injection during aortofemoral bypass surgery and cardiopulmonary bypass procedures. One example of a low molecular weight heparin currently being marketed is Logiparin (LHN-1, Novo, Denmark). Logiparin is produced from porcine intestinal mucosal heparin by enzymatic depolymerization using heparinase. Its molecular mass ranges from 600 to 20,000 daltons, with more than 70% of its molecular mass ranging between 1,500 and 10,000 daltons. In general, low molecular weight heparins have an improved pharmacokinetic profile as compared to standard, unfractionated heparin, less antiplatelet activity (and, consequently, less bleeding potential), less lipolytic effect, and a half-life which is not dependent on the initial dose administered. Unfortunately, the use of protamine to reverse the anticoagulation effects of LMWH may result in the same undesired side effects produced by its use in connection with standard, unfractionated heparin. Moreover, protamine is known to incompletely reverse the anti-Xa activity of LMWH. There is, therefore, a need in the art for an improved agent for reversing the anticoagulation effects of LMWH.

It is, therefore, an object of this invention to provide improved agents for reversal of heparin anticoagulation.

It is another object of this invention to provide improved agents for reversal of low molecular weight heparin anticoagulation.

It is also an object of this invention to provide improved agents for reversal of heparin or low molecular weight heparin anticoagulation which are relatively easy and inexpensive to synthesize.

It is a still further object of this invention to provide nontoxic, or less toxic, variants of protamine which will adequately reverse the effects of heparin or low molecular weight heparin anticoagulation.

SUMMARY OF THE INVENTION

The foregoing and other objects are achieved by this invention which provides synthetic protamine-like peptides which are useful as heparin or low molecular weight heparin anticoagulation reversal agents. The peptide compositions of the present invention may comprise a sequence of 20–40 amino acids having a total cationic charge of less than the [+21] charge of n-protamine, as determined by the number of positively charged amino acids in the sequence, and the ability to at least partially reverse the effects of heparin or low molecular weight heparin anticoagulation. Preferably, the total cationic charge on the peptide composition is in the range of [+14] to [+18].

In certain preferred embodiments, the distribution of positive residues in the peptide/protein remain similar to naturally-occurring protamine. Charge density, charge distribution and peptide length have been altered as will be described hereinbelow. However, a random or even distribution of positive charges throughout the length is feasible provided that the total charge on the peptide is within the preferred range.

Invariably, arginine is the basic residue of the charged clusters in n-protamine. In the present embodiments, arginine residues have been replaced with lysine residues. Lysine, like arginine, carries a positive charge at physiological pH and is preferably used in the amino acid sequence due to technical difficulties which are encountered in the automated synthesis of multiple arginine-containing peptides. Further, the use of lysine simplifies interpretation of steric effects.

Of course, and positively charged amino acid, such as histidine, arginine or analogs thereof, such as ornithine or methyl arginine, can be used for inserting positive charges into the synthetic protamine-like peptide analogs in accordance with the present invention.

In preferred embodiments, the positively charged amino acids or lysines are arranged into groups of either two or four consecutive residues to simulate the grouped arrangement of arginine residues within the major component of n-protamine. In the embodiments described herein, peptide length has been kept constant at 29 amino acids. However, length can be varied, illustratively from about 20 to 40.

The aminoacyl connecting residues of n-protamine were replaced with glycine residues in order to simplify the structure and to simplify the synthesis and give flexibility to the molecule. Glycine has no side chains to sterically interfere with the charge-charge interaction between the protamine variant compounds and negatively charged heparin.

In advantageous embodiments, lysine residues were selectively replaced with the uncharged amino acid glutamine in order to decrease the number of positive charges on the molecule and to decrease the charge density. Glutamine has a similar hydrophilicity and size/steric configuration to lysine.

In addition to glutamine, any uncharged amino acid, such as alanine, serine, threonine, asparagine, proline, valine, isoleucine, leucine, or analogs thereof, may be used in the preparation of the synthetic peptide analogs of the present invention.

Proline occurs at the terminus of naturally-occurring protamine and has been retained in the embodiments presented herein in order to inhibit the breakdown of the peptide by circulating aminopeptidases. However, it is contemplated that the N- and C-terminus groups can be modified. An amide bond, for example, at the C-terminus might affect resistance to degradation while acetylation at the N-terminus might have a similar effect. These modifications of the N- and C-termini may also effect biological activity and/or toxicity.

We have discovered that the charge on the peptide molecule is directly proportional to the toxicity and the efficacy as an agent for the reversal of the anticoagulation effects of heparin. Therefore, we have developed synthetic protamine-like peptides with lower total cationic charge in order to reduce toxicity effects, but which retain enough positive charge for, at least partial, in vivo reversal of heparin. We have found that a total cationic charge of [+14] to [+21] on the molecule is advantageous for heparin reversal In fact, the total cationic charge (as determined from the number of lysine residues) is a more important factor in heparin anticoagulation reversal than the specific amino acid composition. However, as the total cationic charge on the peptide increases, so does toxicity as measured by adverse hemodynamic effects. In a preferred embodiment of the invention, protamine variants having a charge in the range of [+14] to [+18], and preferably [+16], have an improved efficacy to toxicity ratio for the reversal of heparin anticoagulation.

In preferred embodiments for the reversal of the anticoagulation effects of low molecular weight heparin, protamine variants having a charge in the range of [+16] to [+18] which have been amidated at the C-terminus and acetylated at the N-terminus to prevent in vivo degradation produce particularly efficacious results. In further advantageous embodiments, the number of amino acid residues in the peptide chain should be appropriate to facilitate alpha-helix formation on binding to the low molecular weight heparin, illustratively 28 or 32 in the case of amidated and acetylated compounds having changes of [+16] and [+18], respectively. Using alanine residues in the connecting amino acids between charged clusters increases stability of alpha-helix formation on binding low molecular weight heparin.

L-amino acids have been used in the preparation of the inventive compositions; however, D-amino acids or beta and delta forms may be used, and in fact, these other forms may reduce the levels of degradation in vivo.

In a method aspect of the invention, an anticoagulation-reversing effective amount of a protamine-like peptide analog of the present invention, or a combination of such analogs, is administered to a living being in a suitable parenteral vehicle, for example. Dosage ranges are with the skill of a person of ordinary expertise in the art, illustratively 1:1 peptide:heparin (1 mg/100 IU heparin). As used herein, the term "anticoagulation-reversing effective amount" refers to the amount necessary to produce cessation of clinical bleeding and to cause return of quantitative coagulation tests to their baseline level.

The protamine-like peptide analogs of the present invention are synthesized from L-amino acids. However, the product is a partially racemic mixture which must be resolved and characterized. FDA regulations do not permit more than 50% D-amino acids for human usage. Of course, the peptide analogs should be sterilized prior to administration to humans or animals.

BRIEF DESCRIPTION OF THE DRAWING

Comprehension of the invention is facilitated by reading the following detailed description, in conjunction with the annexed drawing, in which:

FIG. 1a shows activated clotting time (ACT), FIG. 1b shows thrombin clotting time (TCT), FIG. 1c shows Heparin Antifactor Xa Activity, and FIG. 1d shows Heparin Antifactor IIa Activity;

FIG. 2a and FIG. 2b are graphical representations of mean arterial blood pressure and cardiac output changes observed in an in vivo dog model following administration of protamine and selected synthetic protamine-like peptide analogs of the present invention. The data are expressed as percent change from baseline and are plotted against time in seconds.

DETAILED DESCRIPTION OF THE INVENTION

Figure 1A:
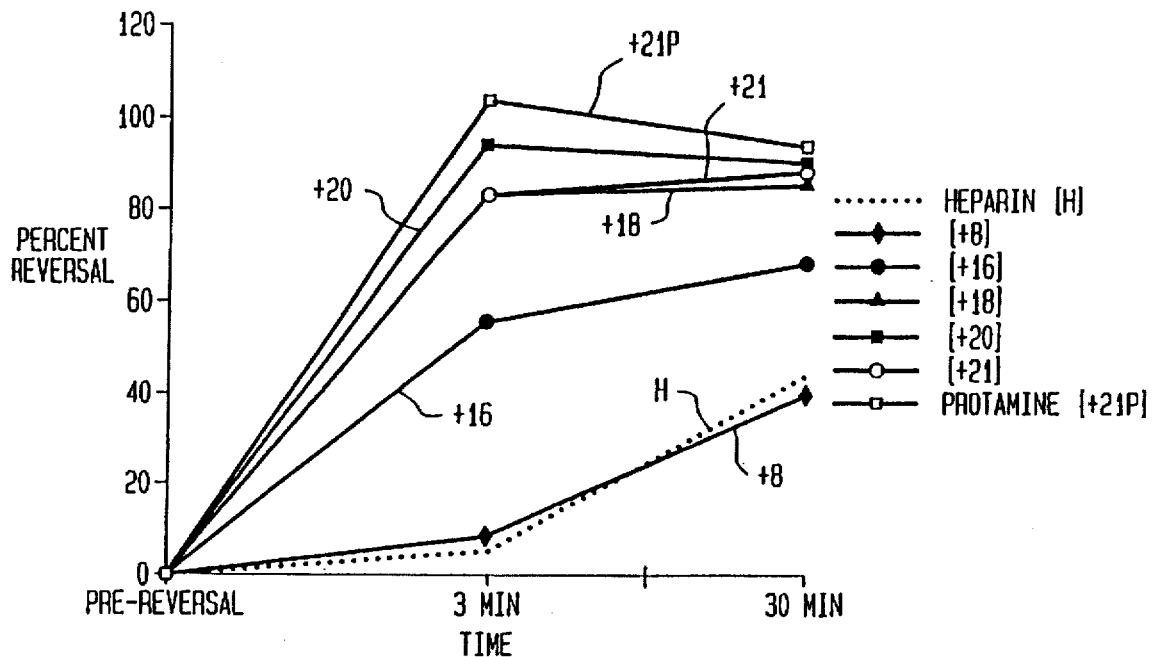
FIG. 1a through FIG. 1d are graphical representations of heparin anticoagulation activities achieved by n-protamine (Protamine [+21]) and selected synthetic protamine-like peptide analogs of the present invention plotted as a percent of reversal against time in minutes, more specifically.

The following definitions are used herein to denote the amino acids comprising the exemplary peptides of the present invention:

P=Pro=proline
K=Lys=lysine
G=Gly=glycine
O=Gln=glutamine
R=Arg=arginine
S=Ser=serine
V=Val=valine
A=Ala=alanine
Y=Thr=threonine Synthesis of Protamine-Like Peptide Analogs Peptides of the present invention can be made by recombinant genetic technology, chemical methods, or protein synthesis techniques, such as automated fluorenyl-methoxycarbonyl (FMOC) and t-butyloxycarbonyl (TBOC) procedures. The resultant products may be purified and characterized by amino acid analysis and mass spectroscopy.

In illustrative embodiments, protamine-like peptide analogs were synthesized with an automated peptide synthesizer using FMOC-amino acids (Applied Biosystems, Model 431). Once synthesized, these peptides were purified on a polysulfoethyl polyaspartamide high pressure liquid chromatography (HPLC) cation exchange column diluted by a sodium sulfate salt gradient (0–0.2 M, pH 3.0), and desalted on a 300 Å pore diameter size exclusion HPLC (1 centimeter by 25 centimeters) using 15% acetonitrile, 50 mM formic acid buffer. Each purified peptide was characterized by amino acid analysis and mass spectroscopy to confirm purity prior to use. Inclusion of norleucine as an internal standard for amino acid analysis allowed accurate assessment of peptide concentration.

The following peptide analogs were synthesized so that the total number of lysine residues determined the total peptide cationic charge as set forth in Table 1. It is to be understood that the peptides listed in Table 1 are merely exemplary of the many different permutations and combinations of amino acids within the contemplation of the principles of the invention.

TABLE 1

| Amino Acid Sequence | ID SEQ NO: | Total X Cationic Charge |
|---|---|---|
| (1) $P(K_2O_2G_4)_3K_2O_2$ | 1 | [+8]* |
| (2) $P(KG)_{13}K$ | 2 | [+14] |
| (3) $YP(KA)_{13}K$ | 3 | [+14] |
| (4) $P(K_4G_4)_3K_4$ | 4 | [+16]* |
| (5) $PK_4G_4(K_4G_2)_3K_2$ | 5 | [+18]* |
| (6) $P(K_2G)_9K_2$ | 6 | [+20] |
| (7) $P(K_4G_2)_4K_4$ | 7 | [+20]* |

TABLE 1-continued

| Amino Acid Sequence | ID SEQ NO: | Total X Cationic Charge |
|---|---|---|
| (8) $PK_4S_3KPVK_5PKVSK_6G_2K_4$ | 8 | [+21]* |
| (9) $PR_4S_3RPVR_5PRVSR_6G_2R_4$ (n-protamine) | 9 | [+21]* |

The peptide, designated (8) in Table 1, having a [+21] charge and the same sequence as n-protamine, was synthesized in order to compare the effect of the sole substitution of lysine for arginine. The peptides designated as (2) and (6) on Table 1 are examples of peptides in which the positive charges are not clustered. Preliminary studies indicate that these peptides exhibit similar efficacy and toxicity effects to the grouped compounds; provided that the total charge on the peptide is maintained in the appropriate range.

I. Studies on the Reversal of the Anticoagulation Effects of Standard Heparin

The ability of the protamine-like peptides of the present invention to reverse the anticoagulation effects of standard, unfractionated heparin was assessed by in vivo canine studies conducted with the peptides marked on Table 1 with an asterisk. in vivo Canine Studies Five female dogs (8–15 kg) received standard, unfractionated heparin (150 IU/kg IV) followed by reversal with either control commercial salmine protamine (n-protamine, [+21]) or one of the five variants listed hereinabove in Table 1 and marked with an asterisk (1.5 mg/kg IV over 10 seconds). As used hereinafter, the peptides will be identified by their total cationic charge value, e.g., [+8], [+16], etc.

Data are expressed as a mean +1 SD. Statistical analysis using linear regression for determination of correlation coefficients, and analysis of variance (ANOVA) or unpaired two-way Student's t-test; $p < 0.05$ was accepted as statistically significant.

Coagulation and Hematologic Studies

Anticoagulation versal was assessed by a number of standard coagulation tests performed upon samples of venous blood: activated clotting time (ACT), prothrombin time (PT), activated padial thromboplastin time (aPTT), thrombin clotting time (TCT), heparin concentration by assay for FXa inhibitory activity (FXa), white cell count (WBC), and platelet counts (PLT). Measurements were made 3 minutes prior to heparin reversal (baseline) and 3 minutes and 30 minutes post-administration of the heparin reversal agent. Reversal of heparin anticoagulation, expressed as the percent change, was calculated and reported in Table 2 hereinbelow. The "Heparin" row sets forth the observed reversal as a consequence of expected heparin metabolism or degradation alone.

TABLE 2

PERCENT REVERSAL OF HEPARIN ANTICOAGULATION
BY VARIANT PEPTIDES AND PROTAMINE

| Charge | ACT 3 min | ACT 30 min | PT 3 min | PT 30 min | APTT 3 min | APTT 30 min | TCT 3 min | TCT 30 min | FXa 3 min | FXa 30 min | FIIa 3 min |
|---|---|---|---|---|---|---|---|---|---|---|---|
| Heparin | 4 | 41 | 5 | 46 | 12 | 66 | 0 | 0 | 3 | 8 | 6 |
| [+8] | 7 | 37 | 21 | 50 | 0 | 50 | 0 | 0 | −1 | 9 | 8 |
| [+16] | 54 | 65 | 73 | 59 | 58 | 56 | 0 | 0 | 23 | 42 | 8 |
| [+18] | 81 | 82 | 74 | 91 | 79 | 80 | 75 | 57 | 60 | 51 | 41 |
| [+20] | 92 | 87 | 83 | 80 | 91 | 91 | 109 | 92 | 83 | 70 | 79 |
| [+21] | 81 | 85 | 97 | 93 | 88 | 85 | 91 | 79 | 55 | 49 | 59 |
| Protamine [+21] | 102 | 90 | 84 | 88 | 100 | 127 | 101 | 100 | 101 | 96 | 102 |

Figure 1B:
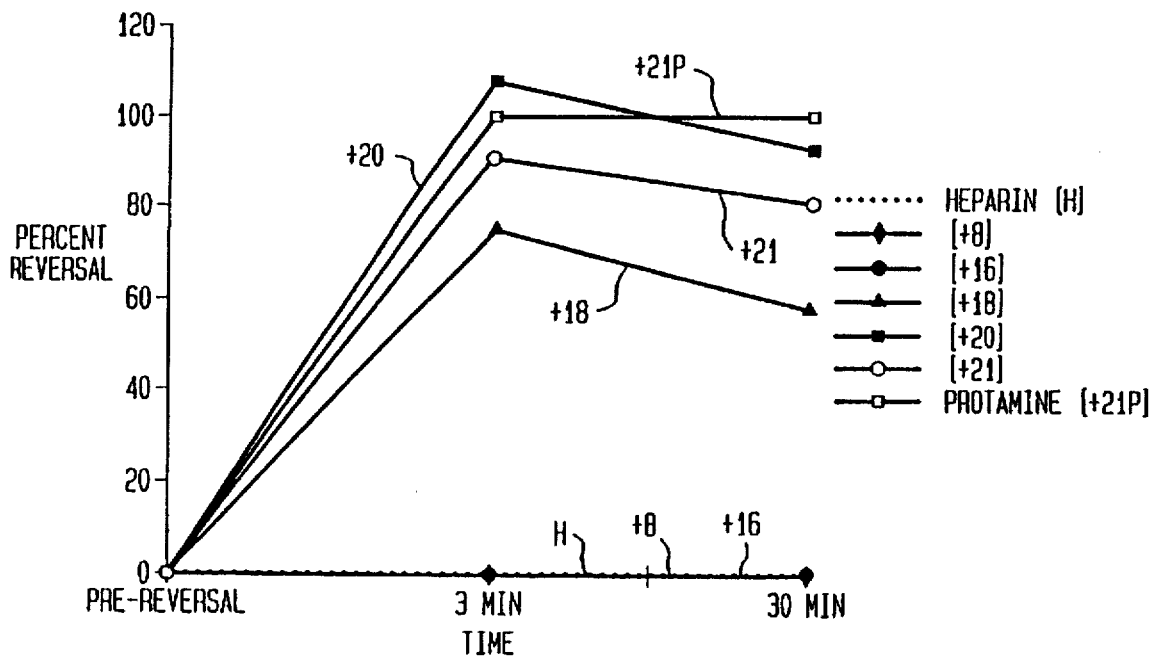
Figure 1C:
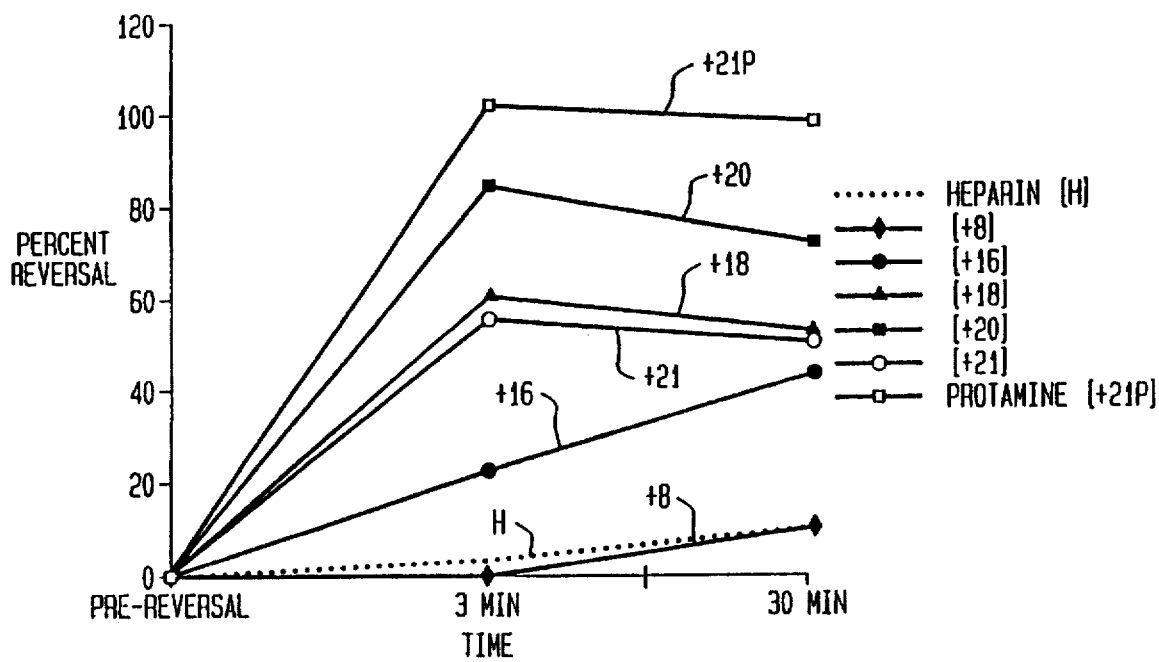
Figure 1D:
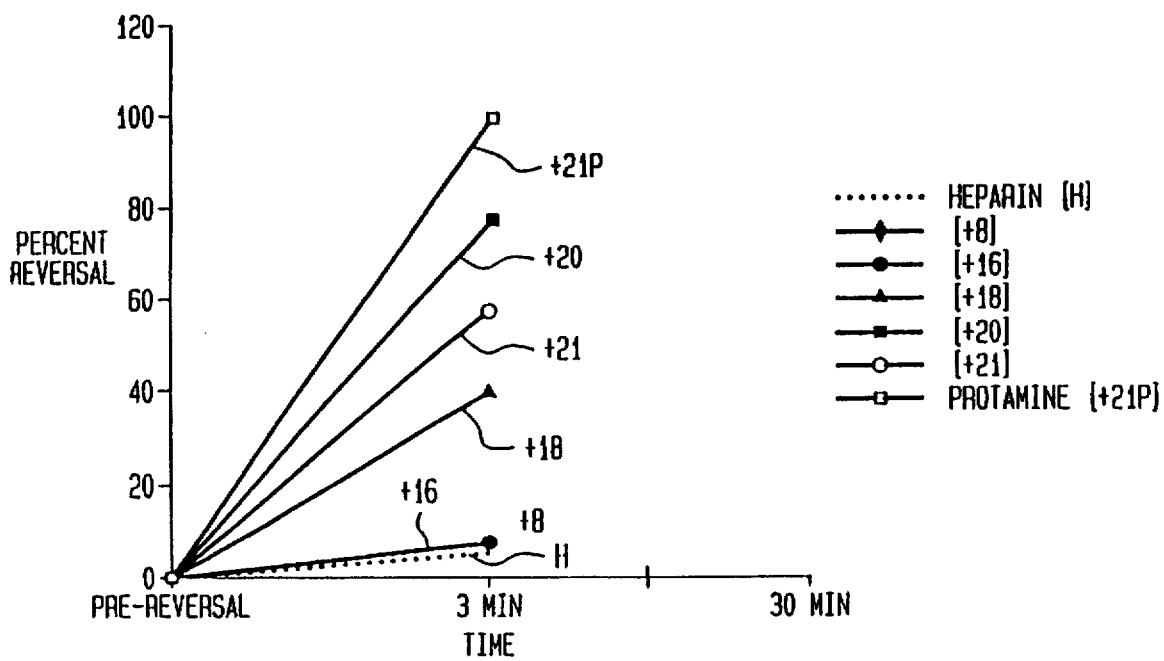

FIG. 1a through FIG. 1d are graphical representations of the heparin anticoagulation activities reported in Table 2. More specifically, FIG. 1a shows activated clotting time (ACT), FIG. 1b shows thrombin clotting time (TCT), FIG. 1c shows Heparin Antifactor Xa Activity, and FIG. 1d shows Heparin Antifactor IIa Activity. Referring to the figures, the [+18] peptide produced a modest amount of reversal of these parameters. Interestingly, [+16], while producing 54% ACT, 58% aPTT, and 23% FXa reversal resulted in no TCT or FIIa reversal above that expected by heparin degradation alone. This finding is noteworthy in that both TCT and FIIa assays measure only the thrombin-dependent portion of the coagulation cascade and, therefore, only the anti-IIa effects of heparin anticoagulation.

Analysis of platelet counts at 3 minutes post-reversal reveals thrombocytopenia with the peptides [+18], [+20], [+21] and [protamine +21], which resolved by about 30 minutes. Despite this trend, a linear correlation between peptide charge and degree of thrombocytopenia at 3 minutes was not observed. Analysis of change in white cell count at 3 and 30 minutes post-reversal also revealed no significant correlation with peptide charge.

Application of linear regression analysis to the data of Table 2 revealed a strong correlation between the percent reversal of heparin anticoagulation and peptide total cationic charge as shown in Table 3. Correlation coefficients relating coagulation studies to charge were generated on percent reversal data corrected for expected percent reversal due to heparin metabolism.

TABLE 3

CORRELATION OF TOTAL CATIONOIC CHARGE TO HEPARIN
REVERSAL AS MEASURED BY SELECTED COAGULATION
STUDIES

|  | 3 min | 30 min |
|---|---|---|
| ACT | 0.97+ | 0.99+ |
| PT | 0.98+ | 0.87* |
| aPTT | 0.99+ | 0.78 |
| TCT | 0.84* | 0.85* |
| FXa | 0.87* | 0.85* |
| FIIa | 0.79** | — |

*p < 0.05
+p < 0.01
**p = 0.06

The ability to reverse heparin as evaluated by these coagulation studies follows a linear relationship except for TCT and FIIa. Minimal TCT and FIIa reversal was noted for the peptide analogs having total cationic charge in the range of [+8] to [+16]. Kinetic studies indicated that the H:AT-III inhibition complex binds to factor IIa with 25 times greater affinity than to factor Xa ($K_D$(M) of $8 \times 10^{-6}$ and $2 \times 10^{-4}$, respectively). Thus, factor IIa may require more positive charge to remove it from the complex. This could explain the observed ability of the [+16] charged peptide to produce partial reversal of ACT, aPTT, and FXa, while producing essentially no reversal of either TCT or FIIa. In addition, kinetic studies have suggested that potentiation of AT-III's anti-IIa effect involves simultaneous binding between heparin and both AT-III and IIa.

Hemodynamic Studies

Hemodynamic studies were conducted by measuring mean arterial pressure (MAP), heart rate (HR), and maximum percent changes in cardiac output (CO) and systemic oxygen consumption ($VO_2$). The results of the hemodynamic studies are shown below in Table 4. Total peptide charge was correlated with observed decreases in MAP, CO and $VO_2$, but not HR.

TABLE 4

EFFECT OF PEPTIDE VARIANTS AND PROTAMINE ON
SELECTED HEMODYNAMIC PARAMETERS

| Charge | ΔMAP | ΔCO | ΔVO$_2$ | ΔHR |
|---|---|---|---|---|
| [+8] | −1 | −8 | −8 | −9 |
| [+16] | −3 | −13 | −10 | −10 |
| [+18] | −31 | −41 | −34 | −17 |
| [+20] | −31 | −40 | −31 | −38 |
| [+21] | −35 | −44 | −38 | −21 |
| protamine [+21] | −34 | −38 | −35 | −29 |

Referring to Table 4, the average maximum decline in MAP in the first five minutes after peptide administration increased with increasing charge. Maximum decreases in MAP, CO and $VO_2$ correlated with total peptide charge with R values of 0.87, 0.87, and 0.86, respectively (significance= $p<0.05$). Further, a trend towards decreasing HR with increasing peptide charge was found but did not achieve significance.

Referring to FIG. 2, the hemodynamic effects followed the same course and pattern for all peptides studied having a positive charge of greater than [+18]. This paralleled the typical response observed for protamine and differed only in the magnitude of hemodynamic changes. FIG. 2a is a classical depiction of the mean arterial pressure plotted as the change from baseline in mm Hg versus time. FIG. 2b is the cardiac output changes from baseline plotted versus time in percent change.

Total toxicity cores (TTS) were developed that reflected maximum declines in each of four parameters (MAP, CO, $VO_2$ and HR) over the first 5 minutes after reversal, the latter being the time of expected greatest adverse hemodynamic effect. The maximum changes occurring in an individual dog over the first 5 minutes were divided by the standard deviation derived from the entire group of tested animals and the four scores were added, resulting in a TTS for each individual dog. The TTS values for each dog were then summed to obtain an average TTS and SD for each peptide studied.

Figure 3:
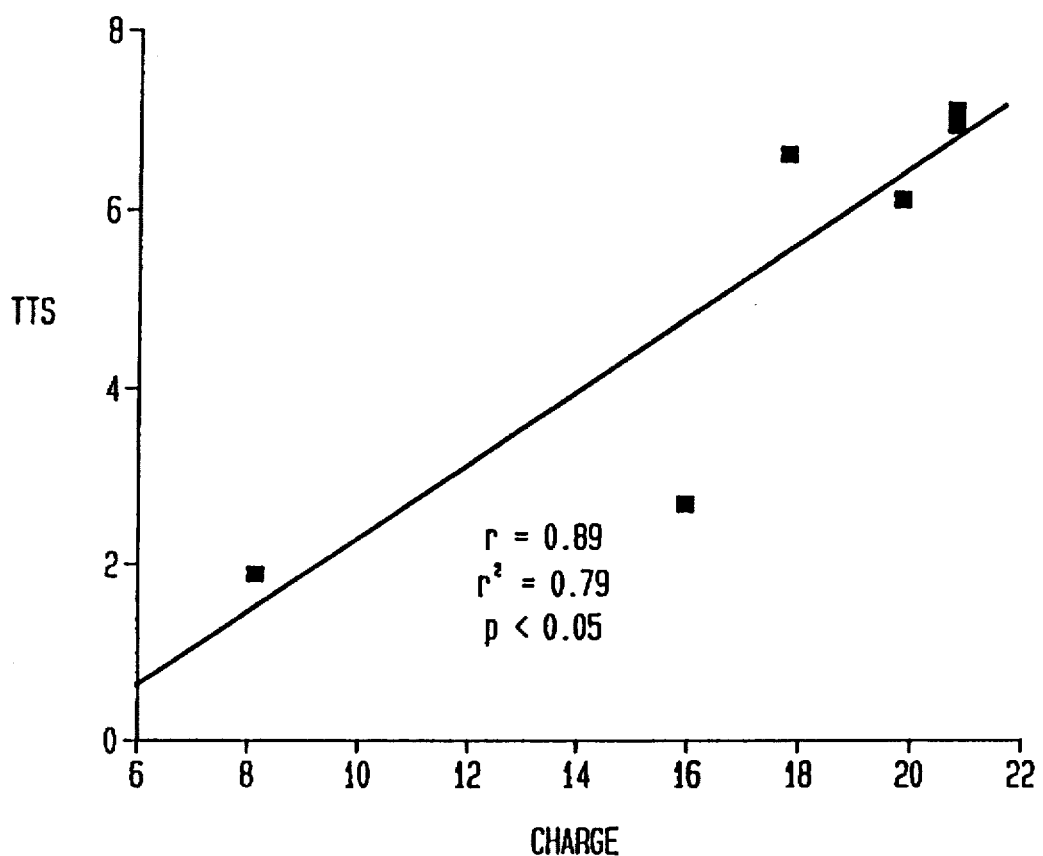
FIG. 3 is a graphical representation of total toxicity scores of selected synthetic protamine-like peptide analogs of the present invention plotted against total cationic charge of the peptide analog.

FIG. 3 is a graphical depiction of the correlation of total toxicity scores to peptide charges. Referring to FIG. 3, the magnitude of the average TTS±SD (expressed as a negative value, i.e., the more negative, the more toxic) was greater with increasing charge: $-1.9\pm1.1$ [+8], $-2.7\pm0.8$ [+16], $-6.6\pm3.3$ [+18], $-6.1\pm3.5$ [+20], $-6.9\pm3.8$ [+21], and $-7.0\pm5.2$ [protamine, +21]. There is a strong correlation between TTS and total cationic charge (R=0.89, p<0.05).

While peptides of [+14] charge were not used to generate the data reported in connection with the in vivo canine studies described hereinabove, other studies were conducted which demonstrated that the [+14] charged peptides had an effect on anticoagulation tests which was intermediate to that of the [+8] and [+16] peptides. The toxicity of the [+14] peptides was equal to or better than the toxicity of the [+16] peptide.

To summarize, the studies confirm that in vivo heparin reversal depends on the availability of positive charges on the molecules. Moreover, these positive charges do not have to be contributed by arginine. Increasing positive charge increases the ability of the synthetic protamine-like peptide to reverse heparin anticoagulation. Although nearly complete reversal of the anticoagulation effects of heparin is achieved with peptides having a charge of [+20] or [+21], the peptide with [+8] charge was not capable of effective heparin reversal. However, reducing the total positive charge from [+21] results in a lower toxicity. There is a difference in toxicity between a peptide with a total cationic charge of [+16] and those charged with [+18] or greater. Thus, peptides of total cationic charge ranging from [+14] to [+18] exhibit a partial ability to reverse the effects of heparin, but have reduced toxicity.

II. Studies on the Reversal of the Anticoagulation Effects of Low Molecular Weight Heparins The ability of the protamine-like peptides of the present invention to reverse the anticoagulation effects of LMWH was assessed in a canine model using four model compounds of charges between [+16] and [+18] as set forth in Table 5 hereinbelow. Standard n-protamine was used as a control.

TABLE 5

| Amino Acid Sequence | SEQ ID NO: | Total X Cationic Charge |
|---|---|---|
| (1) $P(AK_2A_2K_2)_4$ | 10 | [+16] |
| (2) acetyl-$P(AK_2A_2K_2)_4$-amide | 11 | [+16B] |
| (3) $PK(K_2A_2K_2A)_3K_2AK_3$ | 12 | [+18] |
| (4) acetyl-$PA(K_2A_2K_2A)_4K_2$-amide | 13 | [+18B] |
| (5) $PR_4S_3RPVR_5PRVSR_6G_2R_4$ (n-protamine) | 9 | [+21] |

In these embodiments, the aminoacyl connecting residues of n-protamine were replaced with alanine residues in an effort to increase stability of alpha-helix formation on binding to LMWH. The peptide length was made constant at 29 amino acids, and positive charge was calculated by counting lysine (K) residues. In the embodiments labeled "B," e.g., [+16B] and [+18B], the peptide has been amidated at the C-terminus and acetylated at the N-terminus to mitigate against in vivo degradation by carboxypeptidases and amino-peptidases, respectively. The "B" compounds have peptide lengths of 29 or 32 amino acid residues, reflecting the necessary addition of three amino acid residues in order to maintain optimal spacing for alpha-helix formation on binding to heparin. The acetyl and amide moieties also contribute to alpha helix stability by increasing the helical dipole moment.

The protamine-like peptides used in these studies were synthesized on an automated peptide synthesizer using FMOC-amino acids (Applied Biosystems Model 431 synthesizer, Applied Biosystems, Foster City, Calif.) as described hereinabove. In the specific illustrative embodiments set forth in Table 5, the peptides were synthesized in the automated synthesizer on preloaded Wang resins or on RINK resin with 9-fluorenylmethoxycarbonyl amino acid derivatives. The hydroxybenzotriazolyl esters of the 9-fluorenylmethoxycarbonyl-amino acids were formed using 2-(1H benzotriazol-1-yl)-1,1,3,3-tetramethyluronium hexafluorophosphate as an activation agent. Coupling and deprotection of the nascent peptide chains were accomplished under standard conditions for the synthesizer (FastMOC cycles). Cleavage and final deprotection were in 90% trifluoroacetic acid containing 5% ethanedithiol, 2.5% thioanisole, and 2.5% anisole for 2 hours at room temperature. The peptides were precipitated from the trifluoroacetic acid by 20 volumes of diethylether at $-20°$ C. Once synthesized, the peptides were purified by reversed-phase high performance liquid chromatography (HPLC) on a 2"×25 cm preparative reversed-phase column (Rainin, Dynamax, * *). The flow rate was 17 ml/min: and the gradient was from 5% to 60% acetonitrile in 90 minutes. In some instances, the peptides were subsequently described on Sephadex G15 (Pharmacia, Piscataway, N.J.) gel filtration columns equilibrated with 1N acetic acid. Each purified peptide was characterized by amino acid analysis, analytical reversed-phase HPLC, and mass spectroscopy to confirm purity before use. Inclusion of norleucine as an internal standard allowed accurate assessment of peptide concentration. in vivo Canine Studies Seven female dogs (mean weight 12.3 kg) received intravenous LMWH (LHN-1, Logiparin, Novo, Denmark; 150 IU/kg factor Xa activity) followed by reversal with commercial salmine protamine (n-protamine purchased from Eli Lilly, Indianapolis, Ind., 1.5 mg/kg (100 IU/mg) IV) or one of the four variants listed hereinabove at Table 5 after 30 minutes.

Coagulation and Hematologic Studies

Anticoagulation reversal was assessed by a number of standard coagulation tests performed upon samples of venous blood: activated clotting time (ACT), heparin concentration by assay for FXa inhibitory activity (FXa), thrombin clotting time (TCT), and heparin concentration by assay for FIIa inhibitory activity (FIIa). Measurements were made 3 minutes prior to heparin reversal (baseline) and 3 minutes, 10 minutes, and 30 minutes post-administration of the heparin reversal agent. Reversal of LMWH anticoagulation, expressed as the percent change, was calculated and reported in Table 6 hereinbelow. Changes in LMWH anticoagulation occurring from metabolism alone were determined from measurements obtained on a group of five dogs which were not given a reversal agent. The coagulation data were corrected for naturally occurring metabolism.

TABLE 6

PERCENT REVERSAL OF LOW MOLECULAR WEIGHT HEPARIN
ANTICOAGULATION BY VARIANT PEPTIDES AND PROTAMINE

| Charge | ACT | | | FXa | | | TCT | | | F IIa | | |
|---|---|---|---|---|---|---|---|---|---|---|---|---|
| | 30 min | 10 min | 30 min | 3 min | 10 min | 30 min | 3 min | 10 min | 30 min | 3 min | 10 min | 30 min |
| [+16] | 26 | 55 | 78 | 25 | 19 | 29 | 66 | 32 | 50 | 43 | 7 | 44 |
| [+16B] | 62 | 69 | 80 | 48 | 32 | 43 | 97 | 81 | 87 | 77 | — | 69 |
| [+18] | 49 | 52 | 61 | 21 | 17 | 24 | 91 | 67 | 64 | 36 | 24 | 46 |
| [+18B] | 87 | 93 | 102 | 64 | 34 | 52 | 99 | 95 | 96 | 96 | 72 | 74 |
| Protamine [+21] | 99 | 88 | 82 | 63 | 45 | 44 | 100 | 98 | 96 | 99 | — | 86 |

In addition to the measurements reported on Table 6, studies were conducted to measure the activated partial thromboplastin time (aPTT), platelet count, and white blood cell count. There was little to no reversal of aPTT values by the [+16] and [+18] variants, and in fact, both produced a paradoxical increase in aPTT at 3 minutes. However, the [+18B] variant produced greater aPTT reversal than protamine at the 3, 10 and 30 minute measurements (64%, 95%, and 73%, respectively, as compared to 50%, 83%, and 78%, respectively, for protamine). No decrease in thrombocytopenia was observed for the [+18B] variant which has a mean decline in platelet count of −56% as compared to the mean decline in platelet count of −43% observed for protamine. However, the [+16] and [+18] variants exhibited a substantial decrease in thrombocytopenia with mean declines in platelet count of −24% and −8%, respectively. The decline in white blood cell count was found to be the greatest for the [+18B] variant.

The data demonstrate that the protamine-like peptides of the present invention effectively reverse the effects of LMWH. In the case of [+18B], reversal occurs to a degree approaching the efficacy of standard protamine. However, the variants of the present invention are much less toxic than protamine, as will be described hereinbelow in connection with their total toxicity score (TTS).

Hemodynamic Studies

Hemodynamic studies were conducted by measuring mean arterial pressure (MAP) in mm Hg, maximum percent changes in cardiac output (CO) and systemic oxygen consumption ($VO_2$), and heart rate (HR) in beats per minute. The results of the hemodynamic studies are shown below in Table 7. Measurements and calculations were made at baseline, before LMWH administration, 3 minutes before reversal, every 30 seconds for 5 minutes after reversal, and at 10, 20, and 30 minutes after reversal.

TABLE 7

EFFECT OF PEPTIDE VARIANTS AND PROTAMINE ON
SELECTED HEMODYNAMIC PARAMETERS FOLLOWING
ADMINISTRATION OF LOW MOLECULAR WEIGHT HEPARIN

| Charge | ΔMAP | ΔCO | $ΔVO_2$ | ΔHR |
|---|---|---|---|---|
| [+16] | −6 | −8 | −10 | −7 |
| [+16B] | −19 | −18 | −16 | −17 |
| [+18] | −1 | −3 | −4 | −1 |
| [+18B] | −10 | −18 | −12 | −9 |
| protamine [+21] | −32 | −32 | −26 | −18 |

In addition to the foregoing, maximum mean increases in pulmonary artery systolic (PAS) and diastolic (PAD) pressures following administration of protamine were +10 mm Hg and +10 mm Hg, respectively. All of the protamine-like peptides of the present invention were observed to produce greatly decreased responses for both PAS and PAD (+1 mm Hg for the [+16] and [+18] variants and no increase for the [+16B] and [+18B] variants).

Total toxicity scores (TTS) were developed that reflected maximum declines in each of four parameters (MAP, CO, $VO_2$ and HR) over the first 5 minutes after reversal. The maximum changes occurring in an individual dog over the first 5 minutes were divided by the standard deviation derived from the entire group of tested animals and the four scores were added, resulting in a TTS for each individual dog. The TTS valves for each dog were then summed to obtain an average TTS and SD for each peptide studied. The more negative the value of TTS, the more toxic the compound. The TTS for the protamine-like peptide variants of Table 5 are set forth in Table 8.

TABLE 8

| Charge | Total Toxicity Score |
|---|---|
| [+16] | −2.8 ± 2.0* |
| [+16B] | −4.27 ± 1.1* |
| [+18] | −1.3 ± 1.0** |
| [+18B] | −4.1 ± 1.6*** |
| [+21] n-protamine | −7.6 ± 4.8 |

*$p < 0.05$;
**$p < 0.01$;
***$p = 0.084$

Referring to Table 8, the [+16] and [+18] variants are significantly less toxic than protamine. While the [+16B] and [+18B] variants are also less toxic than protamine, the difference is not statistically significant. However, the efficacy of these variants, particularly [+18B], as shown in Tables 6 and 7, is substantially the same as, or better than, protamine in reversing the anticoagulation effects of LMWH. Moreover, the [+18B] variant was actually more effective than protamine by aPTT measurements.

Dose-response studies were conducted. A 50% less dose (1:2 versus 1:1 peptide to LMWH) of [+18B], for example, lowers TTS to about −1.62. Of course, the ability of the peptide to reverse the anticoagulation effects of the LMWH is lowered as well. However, a person of ordinary skill in the art can adjust the dose to achieve an acceptable level of reversal and to minimize toxicity.

The data clearly demonstrate that synthetic protamine-like peptides, in accordance with the present invention, reverse LMWH anticoagulation and are less toxic than protamine. Further, modification of the N- and C-termini to prevent in vivo degradation improves the efficacy of the synthetic protamine-like peptides in reversing the anticoagulation effects of LMWH to a level substantially equaling, and in some cases exceeding, the efficacy of protamine.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A peptide composition comprising a peptide having a sequence of 20–40 uncharged and charged amino acids having a total cationic charge of less than [+21], but not lower than [+14], as determined by the number of positively charged amino acids in the sequence, the uncharged amino acids being selected from the group consisting of glycine, glutamine, serine, threonine, asparagine, proline, valine, and isoleucine, and the ability to at least partially reverse the effects of heparin and/or low molecular weight heparin anticoagulation; and a parenteral vehicle.

2. The peptide composition of claim 1 wherein the total cationic charge is in the range of [+14] to [+18].

3. The peptide composition of claim 2 wherein the total cationic charge is [+16].

4. The peptide composition of claim 1 wherein the positive charges are grouped in clusters which are separated by neutral amino acids.

5. The peptide composition of claim 4 wherein the sequence comprises 29–32 amino acids and the positive charges are grouped in 4 to 5 clusters of 2 to 4 positively charged amino acids are separated by 2 to 6 neutral amino acids so that the total charge on the polycationic peptide composition is in the range of [+14] to [+18].

6. The peptide composition of claim 1 wherein the positive charges are distributed evenly along the peptide sequence.

7. The peptide composition of claim 1 wherein the positive charges are distributed randomly along the peptide sequence.

8. The peptide composition of claim 1 wherein the positively charged amino acid residue is selected from the group consisting of lysine, histidine, or analogs thereof.

9. The peptide composition of claim 1 wherein the positively charged amino acid residue is lysine.

10. The peptide composition of claim 1 wherein the uncharged amino acid residues are glutamine.

11. The peptide composition of claim 1 wherein the uncharged amino acid residues are glycine.

12. The peptide composition of claim 1 wherein the sequence of amino acids has a C-terminus and an N-terminus at least one of which is modified to be resistant to in vivo degradation.

13. The peptide composition of claim 12 wherein the C-terminus of the sequence of amino acids is amidated.

14. The peptide composition of claim 12 wherein the N-terminus of the sequence of amino acids is acetylated.

15. A polycationic peptide composition comprising a peptide having a sequence of about 29 to 32 amino acid residues wherein 4 to 5 clusters of 2 to 4 positively charged amino acids are separated by 2 to 6 neutral amino acids so that the total charge on the polycationic peptide composition, which is determined by the number of positive amino acids in the sequence, is in the range of [+14] to [+18]; and a parenteral vehicle.

16. The polycationic peptide composition of claim 15 wherein the charge is [+16].

17. The polycationic peptide composition of claim 15 wherein the sequence of amino acids has a C-terminus and an N-terminus at least one of which is modified to be resistant to in vivo degradation.

* * * * *